United States Patent
Medley

(10) Patent No.: US 7,604,736 B2
(45) Date of Patent: Oct. 20, 2009

(54) LASER WELDED FRIT

(75) Inventor: Michael L Medley, Beverly Hills, FL (US)

(73) Assignee: Optimize Technologies, Inc., Oregon City, OR (US)

( * ) Notice: Subject to any disclaimer, the term of this patent is extended or adjusted under 35 U.S.C. 154(b) by 289 days.

(21) Appl. No.: 11/042,852

(22) Filed: Jan. 24, 2005

(65) Prior Publication Data

US 2005/0161382 A1    Jul. 28, 2005

Related U.S. Application Data

(60) Provisional application No. 60/538,617, filed on Jan. 22, 2004.

(51) Int. Cl.
    *B01D 15/08* (2006.01)

(52) U.S. Cl. .................. 210/198.2; 210/656; 96/101

(58) Field of Classification Search .......... 210/656, 210/198.2, 232, 450, 456, 541; 96/101, 105, 96/107
    See application file for complete search history.

(56) References Cited

U.S. PATENT DOCUMENTS

| | | | | |
|---|---|---|---|---|
| 4,399,032 A | * | 8/1983 | Mott | 210/198.2 |
| 4,457,846 A | * | 7/1984 | Munk | 210/656 |
| 4,469,496 A | * | 9/1984 | Frischmuth et al. | 96/104 |
| 4,469,597 A | * | 9/1984 | Mott | 210/198.2 |
| 4,713,520 A | * | 12/1987 | Van Nice et al. | 219/121.63 |
| 5,089,125 A | * | 2/1992 | Hart et al. | 210/198.2 |
| 5,137,628 A | * | 8/1992 | Hart et al. | 210/198.2 |
| 5,997,746 A | * | 12/1999 | Valaskovic | 210/656 |
| 6,224,775 B1 | * | 5/2001 | Foley et al. | 210/635 |
| 6,427,846 B1 | * | 8/2002 | Graus et al. | 210/445 |
| 6,432,307 B2 | * | 8/2002 | Gizowski et al. | 210/321.6 |
| 6,527,951 B1 | * | 3/2003 | Tuvim | 210/198.2 |
| 6,896,753 B2 | * | 5/2005 | Memmer | 156/73.5 |
| 2002/0056676 A1 | * | 5/2002 | Tuvim | 210/198.2 |
| 2003/0205515 A1 | * | 11/2003 | Purdom et al. | 210/198.2 |
| 2005/0045543 A1 | * | 3/2005 | Gjerde et al. | 210/198.2 |
| 2006/0213823 A1 | * | 9/2006 | Rigoli | 210/198.2 |

OTHER PUBLICATIONS

Snyder, Introduction to Modern Liquid Chromatograph, John Wiley & Sons, Inc. 1979, pp. 204-206.*

* cited by examiner

*Primary Examiner*—Ernest G Therkorn
(74) *Attorney, Agent, or Firm*—Christensen O'Connor Johnson Kindness PLLC

(57) ABSTRACT

A method of forming a column (100 and 200) for use with an analytical chemical instrument. The method includes placing a frit (102 and 202) in proximity to a distal end (110 and 210) of a tube (104 and 204) having an internal bore (106 and 206) adapted to receive packing material (108 and 208) for selectively interacting with an analyte of interest in a sample. The method further includes laser welding the frit to the tube and inserting packing material within the internal bore of the tube. A column formed in accordance with this method.

9 Claims, 3 Drawing Sheets

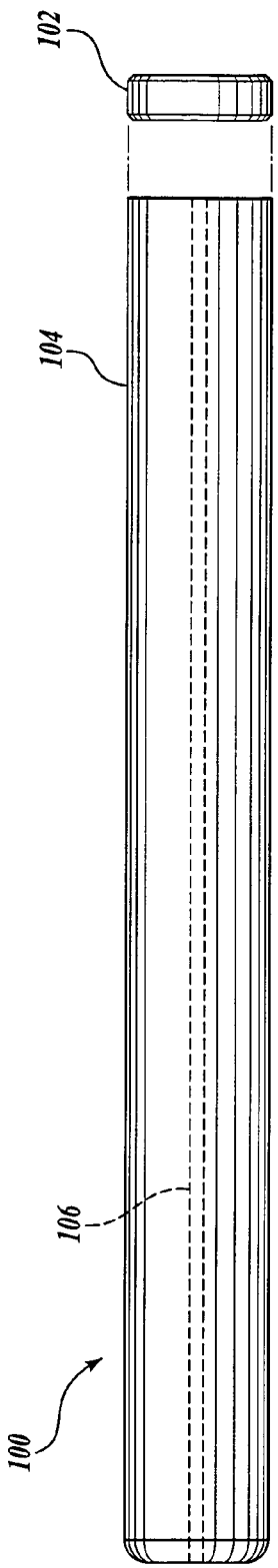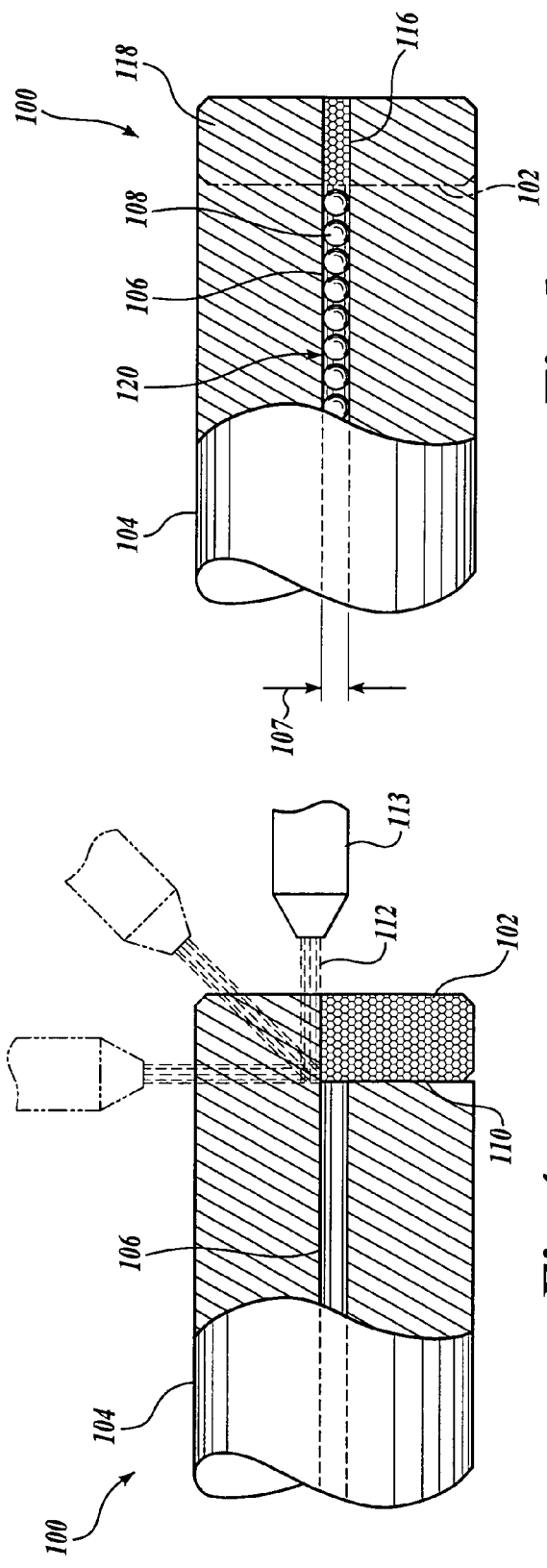

LASER WELDED FRIT

CROSS-REFERENCE TO RELATED APPLICATION

This application claims the benefit of U.S. Provisional Application No. 60/538,617, filed Jan. 22, 2004, and entitled Laser Welded Frit, the disclosure of which is hereby expressly incorporated by reference.

FIELD OF THE INVENTION

The present invention relates to columns for use with an analytical chemical instrument, the column adapted to receive packing material for selectively interacting with an analyte of interest in a sample, and more specifically to columns and methods of forming columns having a frit which is welded to a tube of the column.

BACKGROUND OF THE INVENTION

A number of chemical analytical techniques utilize columns for detecting or measuring an analyte of interest. The columns each include a cylindrical tube of a particular length and inner diameter dictated by experimental requirements that are filled with selectively adsorbent packing materials. An analyte or mixture of analytes (the "sample") dissolved in a solution (the "sample matrix") is introduced at one end of the column, and then a carrier fluid is run through the column. The carrier fluid brings the sample matrix along with it.

As analytes travel through and around the column packing material, the analytes interact with the column packing material to varying degrees according to the analytes' chemical affinity for the packing material. The greater the affinity of a particular analyte for the packing material, the longer it will take for that analyte to travel the length of the column. Analytes that have no affinity whatsoever for the packing material will travel at approximately the same speed as the carrier solvent, while analytes with affinity for the packing material will be delayed by an amount generally proportional to that affinity. Therefore, a single analyte in solution can be separated from its sample matrix, or a mixture of analytes in solution can be separated both from the sample matrix and from each other, based on differing affinities for a given packing material. Such techniques are used in liquid chromatography (LC) as well as in situations where LC is combined with other instrumentation (liquid chromatography-mass spectrometry, or LCMS, for example).

Most packing materials include either regular (spherical) or irregular particles, with a predetermined nominal diameter. Actual particle diameters are likely to be within a normal distribution around this predetermined nominal diameter. A design requirement of chromatography column hardware is that the hardware must allow liquids to pass into and out of the column, while keeping the packing material immobilized within the column tube. This is often accomplished by use of a porous substance called a "frit" disposed at an inlet end and at an outlet end of the column. This frit has a rated porosity that is smaller than that of the smallest expected packing material particles.

The outlet frit of a column is more than just a barrier for keeping packing material in place. The frit actually plays an important role in determining overall column performance. Packing materials, particularly those that are formed from regular, spherical particles, must be placed into a column in a way that ensures the packing material is tightly packed and evenly distributed, without voids, channels, and other irregularities. Any deviance from a perfectly packed bed will reduce the effective separating power and performance of the analytical column. Columns are packed by sending packing material slurry through the column, which is open at the inlet. The slurry solvent passes through the outlet frit, while the packing material collects at the frit surface, gradually filling the column. And so the outlet frit is actually the foundation upon which the packed bed is built. Thus, the method used to retain the frit at the column outlet is preferably mechanically durable. It is also preferable that the seal between the frit and the column be as close to hermetic as practically possible. This ensures that the only possible flow path out of the column is through the frit. Internal volumes should also be kept as low as possible to minimize "mixing" effects, which can serve to decrease instrument sensitivity and response.

Previously developed columns are manufactured with one of a few methods for keeping outlet frits in place. A frit can be placed at the surface of a tube and secured via an external compression fitting. Or, the frit can be placed within the tube diameter and secured there. This second approach is desirable in terms of keeping internal volumes to a minimum.

Current methods employed in securing frits within the inner diameter of column tubes include:

Interference fit, where the diameter of the frit is selected to be slightly larger by a precise amount than the inner diameter of the tubing, and the frit is forcibly pressed into the smaller cavity, resulting in a friction fit;

Adhesive bonding, where a chemical adhesive is used to provide a bond between the frit and the inner tube wall;

Staking, either a roll-stake or orbital stake method, where the frit is placed within a counter-bored cavity with a thin wall at the end of the tube, and this thin walled material is then rolled over the side and front edge of the frit;

Sintering, where the frit is actually produced in situ within the tube end, rather than being manufactured separately;

Controlled atmosphere brazing, where the frit is brazed onto the end of tube in a controlled atmosphere; and Welding, where, referring to FIG. 1, a frit 12 is welded onto a distal end of a tube 14 to form a column 10. This is accomplished by inserting a porous frit 12 into a recess 16 disposed in a distal end of the tube 14. A ring of solder 18, such as silver, is placed along an upper edge of an annular space 20 disposed between the frit 12 and the tube 14. The column 10 is placed in an inert environment and heated, such as by placing the column 10 in an oven, to cause the solder 18 to melt. The melted solder 18 flows in the annular space 20 as shown in FIG. 2. As the solder 18 cools, the outer surface of the frit 12 is bonded to the inner surface of the tube 14 by the solder 18.

The current trend in column hardware technology is toward smaller bed volumes. It is typical for a given sample to be present in very low amounts, or in very low concentrations. Keeping internal volume to an absolute minimum is necessary to avoid dilution of the sample during analysis. Some of the above methods of frit retention are not amenable to use in low-volume applications, while others have limitations and drawbacks of a different kind. Problems of previously developed frit coupling techniques include:

Sample contamination potential from the adhesives used to adhere the frit to the tube;

Non-hermetic seal formed when the frit is attached using staking and interference fit techniques;

Residue left within the tube when in situ sintering techniques are used; and

Referring to FIG. 2, when welding frits 12 to tubes 14 using previously developed welding techniques, the welding must occur in an inert environment to prevent welding residues from contaminating the column 10, thereby increasing the difficulty and expense of welding the frit 12 to the tube 14. Further, it has been found that previous welding techniques are imprecise and unsuitable for frit 12 diameters less than about 0.25 of an inch since the flow of the solder 18 cannot be accurately controlled and may flow into a central bore 22 of the tube 14 interfering with a flow of a sample through the column 10. Further, previously developed welding techniques do not substantially reduce the porous volume of the frit 12 since the solder 18 only adheres to the outer surface of the frit 12 and does not fill in more than a negligible amount, if any, of the pores of the frit 12. Thus, the relatively large porous volume of the frit 12 absorbs a portion of the sample passing through the column 10 creating a dead space in a column 10, thereby introducing error into the testing process and increasing the amount of sample needed to perform the test.

Thus, there exists a need for a column having a frit attached to a tube of the column that is reliable, relatively inexpensive, reduces testing error, and which does not contaminate a sample passing through the column.

SUMMARY OF THE INVENTION

One embodiment of a column formed in accordance with the present invention for use with an analytical chemical instrument, the column adapted to receive packing material for selectively interacting with an analyte of interest in a sample is disclosed. The column includes a tube having a bore adapted to receive a packing material and a distal end. The column also includes a frit coupled to the distal end of the tube for retaining the packing material within the tube while permitting the analyte of interest to pass there through. The column further includes a laser weld coupling the frit to the tube.

One embodiment of a method performed in accordance with the present invention for forming a column for use with an analytical chemical instrument is disclosed. The method includes placing a frit in proximity to a distal end of a tube having an internal bore adapted to receive packing material for selectively interacting with an analyte of interest in a sample. The method further includes welding the frit to the tube and inserting packing material within the internal bore of the tube.

BRIEF DESCRIPTION OF THE DRAWINGS

The foregoing aspects and many of the attendant advantages of this invention will become better understood by reference to the following detailed description, when taken in conjunction with the accompanying drawings, wherein:

FIG. 3 is an exploded elevation view of one embodiment of a column formed in accordance with the present invention showing a frit prior to laser welding of the frit to a distal end of a tube;

FIG. 4 is a partial cross-sectional view of the column of FIG. 3 taken vertically through a centerline of the column showing the frit during laser welding of the frit to the tube;

FIG. 5 is a partial cross-sectional view of the column of FIG. 3 taken vertically through the centerline of the column showing the frit after laser welding of the frit to the tube;

DETAILED DESCRIPTION OF THE PREFERRED EMBODIMENT

Figures 1, 2:
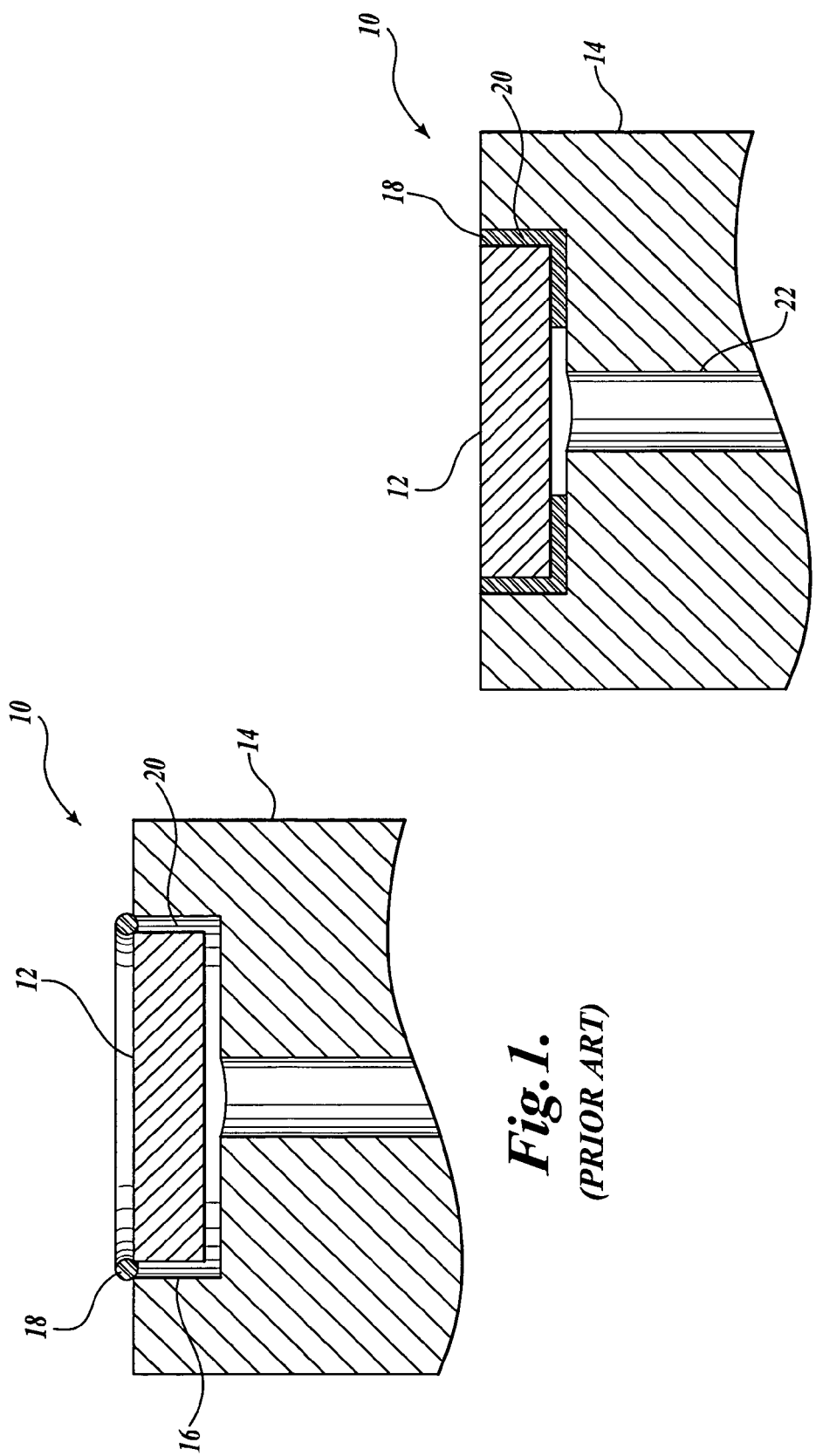
FIG. 1 is a cross-sectional view of a prior art column showing a distal end of a tube prior to melting of a ring of solder.
FIG. 2 is a cross-sectional view of the prior art column of FIG. 1 showing the distal end of the tube after melting of the ring of solder, thereby bonding the frit to the distal end of the tube.

One embodiment of a column 100 formed in accordance with the present invention is shown in FIGS. 3-5. Turning to FIG. 3, the column 100 includes two main components, a frit 102 and a tube 104. The tube 104 is a cylindrical structure of a predetermined length. The tube 104 includes a column bore 106 passing along a centerline of the tube 104. Referring to FIG. 5, the column bore 106 has an inner diameter 107 dictated by experimental requirements for receiving selectively adsorbent packing material 108. In the illustrated embodiment, the bore has a diameter 107 that is approximately 0.006 of an inch, though it should be apparent to those skilled in the art that the diameter of the column bore 106 may be greater or less than the illustrated and described diameter 107, with a few suitable examples being diameters ranging from about 0.002 of an inch to about 0.181 of an inch (4.6 millimeters). The tube 104 may be formed from a rigid material amenable to laser welding, such as a metal, one suitable example being 316L low carbon stainless steel.

The packing material 108 is selected to interact with the analytes of interest to varying degrees according to the analytes' chemical affinity for the packing material. The packing material 108 permits a single analyte in solution to be separated from its sample matrix, or a mixture of analytes in solution to be separated both from the sample matrix and from each other, based on differing affinities for the selected packing material 108. Most packing materials are formed from either regular (spherical) or irregular particles, with a predetermined nominal diameter, one suitable nominal diameter being 5 microns. Of note, for the purpose of clarity, the individual particles of the packing material 108 are greatly enlarged for illustrative purposes in the figures. It should be apparent to those skilled in the art that the particles in an actual embodiment are much smaller relative to the diameter 107 of the column bore 106 than shown in the figures.

The packing material 108 is retained within the bore 106 by the frit 102. The frit 102 allows liquids to pass into and out of the column 100, while keeping the packing material 108 immobilized within the column bore 106 of the tube 104. The frit 102 is formed from a porous material and has a rated porosity that is smaller than that of the smallest expected packing material particles 108 such that the packing material 108 is retained within the bore 106 while the sample and analyte is allowed to pass through the frit 102. In the illustrated embodiment, the frit 102 is formed from a rigid material amenable to laser welding, such as a sintered metal, one suitable example being 316L low carbon stainless steel having a rated porosity that is smaller than that of the smallest expected packing material particles 108. The frit 102 preferably has an outer diameter substantially equal to that of the tube 104. Although the frit 102 may be of any diameter, the process described herein is suitable with frits having small diameters here before unable to be welded, such as diameters of less than about 0.25 of an inch, one suitable example being diameters less than about 0.1 of an inch.

Referring to FIG. 4, during manufacturing of the column 100, the frit 102 is positioned to abut against a distal, square cut end 110 of the tube 104. A laser beam 112 is directed from a laser beam generator 113 and directed by a beam-directing optic (not shown) to selectively focus the laser beam 112 upon the frit 102 and the distal end 110 of the tube 104 to laser weld the frit 102 to the tube 104. The laser welding of the frit 102 may be performed in a non-inert environment.

Turning to FIGS. 4 and 5, by selectively controlling the spot size and power density of the laser beam 112, a penetration depth and width of the laser beam 112 is precisely controlled. This permits the precise and selective conversion of a volume of the frit 102 from a porous state (the original porous material of the frit 102 prior to application of the laser) to a substantially non-porous state (the laser weld 118 formed by melting porous material of the frit 102). The laser beam 112 is selectively controlled to leave a porous passage 116 through the frit 102 having a diameter substantially equal to the diameter of the bore 106 passing through the tube 104, one suitable example being between about 0.002 inches and about 0.2 inches. Stated in other words, the laser beam fuses the frit 102 to the axial distal end 110 of the tube 104 and closes the pores in the frit 102 where the fusing takes place, converting the porous material of the frit 102 to a substantially non-porous laser weld 118. Once the laser welding process is complete, the diameter of the porous metal of the frit 102 is reduced to approximately the same diameter as the column bore 106.

Further, the porous volume of the frit 102 is greatly reduced by the welding process. Moreover, before laser welding, the volume of the frit is occupied completely by porous material. After welding, the volume of the frit that is porous is reduced by about 10%, 50%, 75%, 90%, or 95% or more, and the remaining volume of the frit 102 is occupied by the substantially non-porous laser weld 118. The performance of the resulting packed bed 120 is vastly improved with the reduced volume of the porous portion of the frit 102 since the sample will be focused in a porous passage passing 116 through the frit 102 having substantially the same diameter 107 as the packed bed 120 keeping band broadening to a minimum.

Once the frit 102 is welded in place, the column 104 is packed by sending packing material slurry through the column, which is open at an inlet. The slurry solvent passes through the frit 12, while the packing material 108 collects at an inboard surface of the frit 102, gradually filling the column bore 106, forming the packed bed 120. Thus, the frit 102 acts as the foundation upon which the packed bed 120 is built. Inasmuch as the frit 102 is laser welded to the tube 104, the coupling of the frit 102 to the tube 104 is mechanically durable. Further, the coupling of the frit 102 to the tube 104 by laser welding provides a seal between the frit 102 and tube 104 that is hermetic. This ensures that the only possible flow path out of the column is through the porous passage 116 in the frit 102. This also helps to ensure that internal volumes are kept as low as possible to minimize "mixing" effects, which can serve to decrease instrument sensitivity and response. This also keeps total flow-through volume to a minimum. Further, the walls of the column bore 106 of the tube 104 above the frit 102 is not altered or affected by the welding process. Additionally, the dead volume between the frit 102 and the tube 104 is minimized since the frit 102 is fused to the tube 104 at the junction of the frit 102 with the tube 104.

Referring to FIG. 5, during use, a sample containing an analyte of interest is injected in the column bore 106 and passed through the packed bed 120. The frit 102 impedes the packing material 108 from leaving the column bore 106 while permitting the sample to pass through the porous passage 116 in the frit 102 to the analytical instrument (not shown) for analysis.

Figure 6:
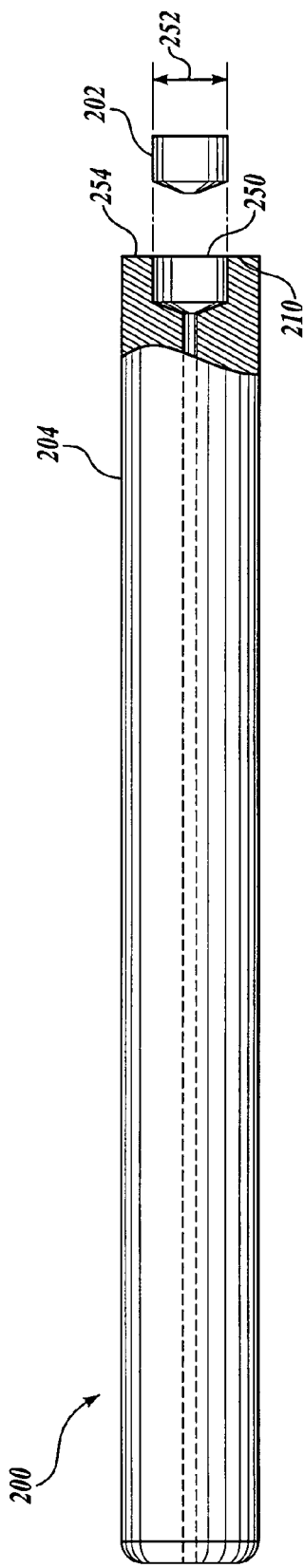
FIG. 6 is an exploded elevation view of an alternate embodiment of a column formed in accordance with the present invention showing a frit prior to laser welding of the frit within a recess disposed in a distal end of a tube.
Figure 7:
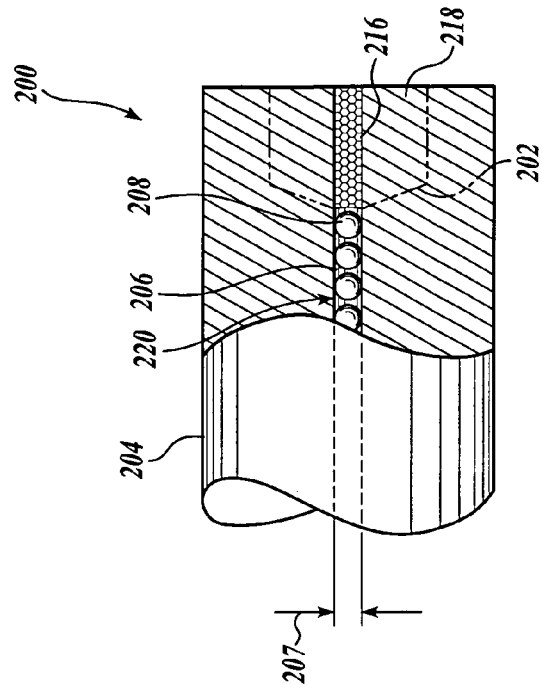
FIG. 7 is a partial cross-sectional view of the column of FIG. 6 taken vertically through a centerline of the column showing the frit during laser welding of the frit within the recess of the tube.
Figure 8:
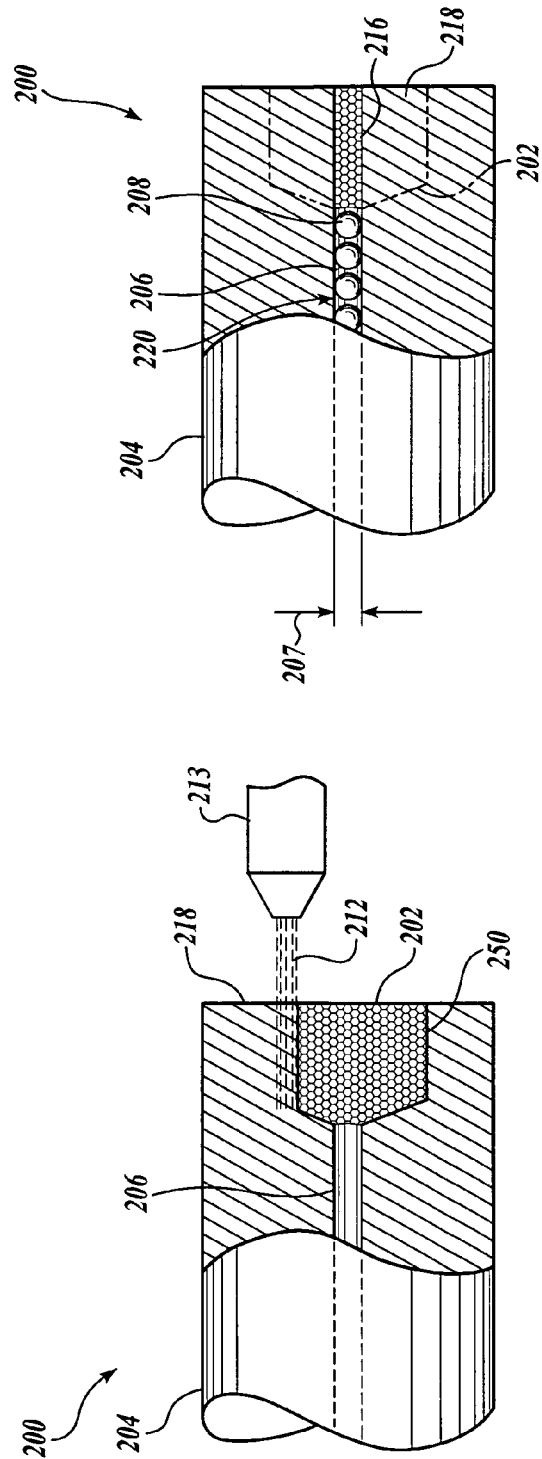
FIG. 8 is a partial cross-sectional view of the column of FIG. 3 taken vertically through the centerline of the column showing the frit after laser welding of the frit within the recess of the tube.

Referring to FIGS. 6-8, an alternate embodiment of a column 200 formed in accordance with the present invention is shown. The column 200 is substantially similar to the column 100 depicted and described in relation to FIGS. 3-5. Therefore, for the sake of brevity, this detailed description will focus only upon the differences between the two embodiments.

Turning to FIG. 6, generally stated, the difference between the embodiment of FIGS. 3-5 and the alternate embodiment of FIGS. 6-8 is that a frit 202 of the column 200 of the alternate embodiment is placed within a recess 250 disposed in a distal end of a tube 204 of the column 200 instead of abutting the frit against a square cut distal end of the tube as is shown and described for the embodiment of FIGS. 3-5. The recess 250 for receiving the frit 202 is preferably cylindrical in shape and may be countersunk as shown in the illustrated embodiment. The frit 202 is correspondingly shaped to be received within the recess 250. Although the frit 202 is illustrated and described as having a countersunk end correspondingly shaped relative to the recess 250, it should be apparent to those skilled in the art that the frit 202 may be alternately shaped, one suitable example being wherein the frit 202 is cylindrical in shape without having a matching frustoconical end to match the countersunk shape of the recess 250 in the tube 204. The frit 202 has a diameter 252 that is less than the outer diameter of the tube 204 such that an annular retaining wall 254 is formed at the distal end 210 of the tube 204 for at least partially housing the frit 202.

Referring to FIG. 7, like the previous embodiment, a laser beam 212 is emitted from a laser beam generator 213 for forming a laser weld 218 for laser welding the frit 202 within the recess 250 and to the tube 204, while leaving a porous passage 216 (see FIG. 8) passing through the frit 202. Turning to FIG. 8, a packing material 208 is then placed within a column bore 206 of the tube 204 to form a packed bed 220 as shown and described above.

The operation of the column 200 of FIGS. 6-8 is identical to the operation of the column 100 of FIGS. 3-5, and therefore for the sake of brevity, will not be redundantly described herein.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A column for use with an analytical chemical instrument, the column adapted to receive packing material for selectively interacting with an analyte of interest in a sample, the column comprising:
   (a) a tube having a bore adapted to receive a packing material and having a distal end; and
   (b) a frit for retaining the packing material within the tube, wherein the frit includes a porous portion that permits the analyte of interest to pass there through, and a substantially non-porous portion made up of a substantially uniform material; and
   (c) a laser weld coupling the frit to the tube, wherein the substantially non-porous portion of the frit defines the laser weld.

2. The column of claim 1, wherein the frit has a width of less than about 0.25 of an inch.

3. The column of claim 1, wherein the frit has a width of less than about 0.1 of an inch.

4. The column of claim 1, wherein the frit includes a porous passageway for permitting the analyte of interest to pass through the frit, and wherein the porous passageway has a diameter substantially equal to a diameter of the bore of the tube.

5. The column of claim 1, wherein the frit includes a porous passageway for permitting the analyte of interest to pass through the frit, and wherein the porous passageway has a diameter between about 0.002 inches and about 0.2 inches.

6. The column of claim 1, wherein the frit has a predetermined volume comprised of the porous portion and the substantially non-porous portion defining the laser weld, wherein the substantially non-porous portion occupies about 10% or more of the predetermined volume.

7. The column of claim 1, wherein the frit has a predetermined volume comprised of the porous portion and the substantially non-porous portion defining the laser weld, wherein the substantially non-porous portion occupies about 50% or more of the predetermined volume.

8. The column of claim 1, wherein the frit has a predetermined volume comprised of the porous portion and the substantially non-porous portion defining the laser weld, wherein the substantially non-porous portion occupies about 75% or more of the predetermined volume.

9. A column for use with an analytical chemical instrument, the column adapted to receive packing material for selectively interacting with an analyte of interest in a sample, the column comprising:

(a) a tube having a bore adapted to receive a packing material and having a distal end; and (b) a frit for retaining the packing material within the tube, wherein the frit includes a porous portion that permits the analyte of interest to pass there through, and a substantially non-porous portion, wherein the porous and non-porous portions are made up of a substantially uniform material; and (c) a laser weld coupling the frit to the tube, wherein the substantially non- porous portion of the frit defines the laser weld.

\* \* \* \* \*

UNITED STATES PATENT AND TRADEMARK OFFICE
CERTIFICATE OF CORRECTION

PATENT NO. : 7,604,736 B2 Page 1 of 1
APPLICATION NO. : 11/042852
DATED : October 20, 2009
INVENTOR(S) : M. L. Medley It is certified that error appears in the above-identified patent and that said Letters Patent is hereby corrected as shown below:

Title Page Item (75) Inventor:  "Michael L Medley," should read
--Michael L. Medley,--

Signed and Sealed this

Sixteenth Day of February, 2010

David J. Kappos
*Director of the United States Patent and Trademark Office*